United States Patent [19]
Matassa et al.

[11] Patent Number: 5,902,819
[45] Date of Patent: May 11, 1999

[54] TRIAZOLE DERIVATIVES

[75] Inventors: Victor Giulio Matassa, Rome, Italy; Francine Sternfeld, London; Leslie Joseph Street, Harlow, both of United Kingdom

[73] Assignee: Merck Sharp & Dohme Ltd., Hoddesdon, United Kingdom

[21] Appl. No.: 08/676,350

[22] PCT Filed: Jan. 24, 1995

[86] PCT No.: PCT/GB95/00134

§ 371 Date: Jul. 19, 1996

§ 102(e) Date: Jul. 19, 1996

[87] PCT Pub. No.: WO95/21166

PCT Pub. Date: Aug. 10, 1995

[30] Foreign Application Priority Data

Feb. 2, 1994 [GB] United Kingdom .................. 9402016

[51] Int. Cl.$^6$ .......................... A61K 31/41; C07D 403/14
[52] U.S. Cl. ........................................ 514/383; 548/266.4
[58] Field of Search .......................... 548/266.4; 514/383

[56] References Cited

FOREIGN PATENT DOCUMENTS

| 497 512 | 5/1992 | European Pat. Off. . |
| 581 538 | 2/1994 | European Pat. Off. . |
| WO 93/18029 | 9/1983 | WIPO . |
| WO 93/21180 | 10/1983 | WIPO . |
| WO 94/02477 | 3/1994 | WIPO . |

*Primary Examiner*—Patricia L. Morris
*Attorney, Agent, or Firm*—Philippe L. Durette; Melvin Winokur

[57] ABSTRACT

Triazole derivatives represented by formula (IIA), and salts and prodrug thereof, wherein $R^1$ represents $C_{1-6}$ alkoxy($C_{1-6}$)alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryloxy($C_{1-6}$)alkyl, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)alkynyl, any of which groups may be optionally substituted; are selective agonist of 5-$HT_1$-like receptors and are therefore useful in the treatment of clinical conditions, in particular migraine and associated disorders, for which a selective agonist of these receptors is indicated.

(IIA)

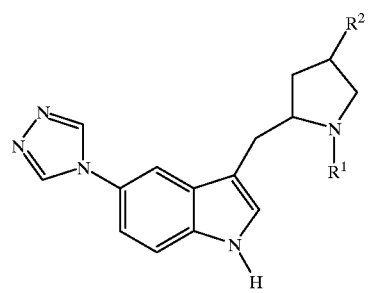

5 Claims, No Drawings

TRIAZOLE DERIVATIVES

This application is a 371 of PCT/GB95/00134 filed Jan. 24, 1995.

The present invention relates to a class of substituted triazole derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

5-HT$_1$-like receptor agonists which exhibit selective vasoconstrictor activity have recently been described as being of use in the treatment of migraine (see, for example, A. Doenicke et al., *The Lancet*, 1988, Vol. 1, 1309–11). The compounds of the present invention, being selective 5-HT$_1$-like receptor agonists, are accordingly of particular use in the treatment of migraine and associated conditions, e.g. cluster headache, chronic paroxysmal hemicrania, headache associated with vascular disorders, tension headache and paediatric migraine.

WO-A-94/02477, published on 3rd February 1994, describes a class of substituted imidazole, triazole and tetrazole derivatives which are stated to be selective agonists of 5-HT$_1$-like receptors and hence to be of particular use in the treatment of migraine and associated conditions.

The present invention provides a compound of formula I, or a salt or prodrug thereof:

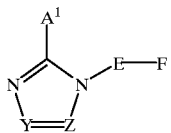

(I)

wherein
one of Y and Z represents nitrogen and the other represents C-A$^2$;

A$^1$ and A$^2$ independently represent hydrogen, hydrocarbon, a heterocyclic group, halogen, cyano, trifluoromethyl, —OR$^X$, —SR$^X$, —NR$^X$R$^y$, —NR$^X$COR$^Y$, —NR$^X$CO$_2$R$^y$, —NR$^X$SO$_2$R$^y$, or —NR$^Z$CTNR$^X$R$^Y$;

E represents a bond or a straight or branched alkylene chain containing from 1 to 4 carbon atoms;

F represents a group of formula

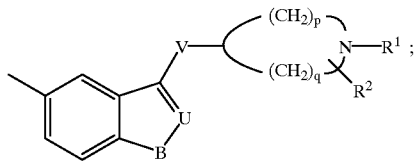

B represents oxygen, sulphur or N—R$^3$;
U represents nitrogen or C—R$^4$;
V represents a straight or branched alkylene chain containing from 1 to 4 carbon atoms;
p is zero or 1 and q is an integer from 1 to 4, provided that the sum of p+q is 2, 3 or 4;
R$^1$ represents C$_{1-6}$ alkoxy(C$_{1-6}$)alkyl, C$_{2-6}$ alkenyl, C$_{2-6}$ alkynyl, C$_{3-7}$ cycloalkyl, C$_{3-7}$ cycloalkyl(C$_{1-6}$)alkyl, aryl, aryl(C$_{1-6}$)alkyl, aryloxy(C$_{1-6}$)alkyl, aryl(C$_{2-6}$) alkenyl, aryl(C$_{2-6}$)alkynyl, C$_{3-7}$ heterocycloalkyl(C$_{1-6}$) alkyl, heteroaryl, heteroaryl(C$_{1-6}$)alkyl, heteroaryl(C$_{2-6}$)alkenyl or heteroaryl(C$_{2-6}$)alkynyl, any of which groups may be optionally substituted;

R$^2$ represents hydrogen, hydrocarbon, a heterocyclic group, halogen, cyano, trifluoromethyl, —OR$^X$, —SR$^X$, NR$^X$R$^y$, —NR$^X$COR$^y$, —NR$^X$CO$_2$R$^y$, NR$^X$SO$_2$R$^y$, —NR$^Z$CTNR$^X$R$^y$, —COR$^X$, —CO$_2$R$^X$, or —CONR$^X$R$^y$;

R$^3$ and R$^4$ independently represent hydrogen or C$_{1-6}$ alkyl;

R$^X$ and R$^y$ independently represent hydrogen, hydrocarbon or a heterocyclic group, or R$^X$ and R$^y$ together represent a C$_{2-6}$ alkylene group;

R$^Z$ represents hydrogen, hydrocarbon or a heterocyclic group;

T represents oxygen, sulphur or a group of formula=N.G; and

G represents hydrocarbon, a heterocyclic group or an electron-withdrawing group.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, aryl and aryl(C$_{1-6}$) alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl and heteroaryl(C$_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

3

A particular aryl group is phenyl.

Particular aryl(C$_{1-6}$)alkyl groups include benzyl, phenethyl and phenylpropyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl groups.

Particular heteroaryl(C$_{1-6}$)alkyl groups include pyridylmethyl and pyrazinylmethyl.

The hydrocarbon and heterocyclic groups, as well as the substituent R$^1$, may in turn be optionally substituted by one or more groups selected from C$_{1-6}$ alkyl, adamantyl, phenyl, halogen, C$_{1-6}$ haloalkyl, C$_{1-6}$ aminoalkyl, trifluoromethyl, hydroxy, C$_{1-6}$ alkoxy, aryloxy, keto, C$_{1-3}$ alkylenedioxy, nitro, cyano, carboxy, C$_{2-6}$ alkoxycarbonyl, C$_{2-6}$ alkoxycarbonyl(C$_{1-6}$)alkyl, C$_{2-6}$ alkylcarbonyloxy, arylcarbonyloxy, C$_{2-6}$ alkylcarbonyl, arylcarbonyl, C$_{1-6}$ alkylthio, C$_{1-6}$ alkylsulphinyl, C$_{1-6}$ alkylsulphonyl, arylsulphonyl, —NR$^V$R$^W$, —NR$^V$COR$^W$, —NR$^V$CO$_2$R$^W$, —NR$^V$SO$_2$R$^W$, —CH$_2$NR$^V$SO$_2$R$^W$, —NHCONR$^V$R$^W$, —CONR$^V$R$^W$, —SO$_2$NR$^V$R$^W$ and —CH$_2$SO$_2$NR$^V$R$^W$, in which R$^V$ and R$^W$ independently represent hydrogen, C$_{1-6}$ alkyl, aryl or aryl(C$_{1-6}$)alkyl, or R$^V$ and R$^W$ together represent a C$_{2-6}$ alkylene group.

When R$^X$ and R$^y$, or R$^V$ and R$^W$, together represent a C$_{2-6}$ alkylene group, this group may be an ethylene, propylene, butylene, pentamethylene or hexamethylene group, preferably butylene or pentamethylene.

When the group G represents an electron-withdrawing group, this group is suitably cyano, nitro, —COR$^X$, —CO$_2$R$^X$ or —SO$_2$R$^X$, in which R$^X$ is as defined above.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

It will be appreciated that the triazole rings of formula I can exist as isomeric forms having differing substitution patterns. These may suitably be represented by formulae IA and IB as follows:

(IA)

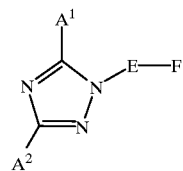

4

-continued (IB)

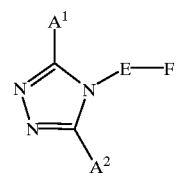

wherein A$^1$, A$^2$, E and F are as defined above.

The alkylene chains E and V may be, for example, methylene, ethylene, 1-methylethylene, propylene or 2-methylpropylene. Alternatively, the group E may represent a single bond such that the group F in formula I is attached directly to the triazole ring.

Suitably, V represents a methylene chain.

The group F is suitably an indole, benzofuran or benzthiophene moiety of formula FA, or an indazole moiety of formula FB:

(FA)

(FB)

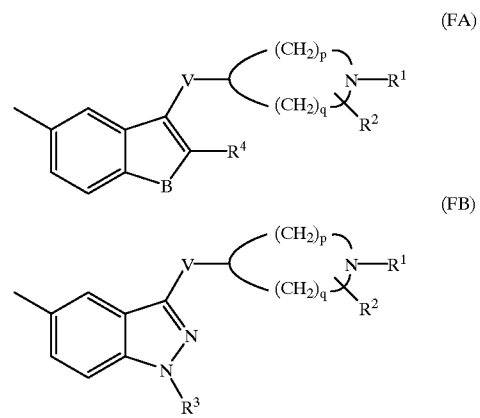

wherein B, V, p, q, R$^1$, R$^2$, R$^3$ and R$^4$ are as defined above. Preferably, the group F represents an indole moiety of structure FC:

(FC)

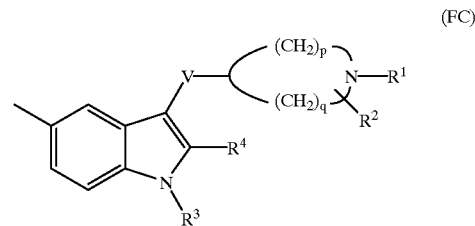

wherein V, p, q, R$^1$ R$^2$, R$^3$ and R$^4$ are as defined above, in particular wherein R$^3$ and R$^4$ are both hydrogen.

Suitable values for the groups A$^1$, A$^2$ and R$^2$ include C$_{1-6}$ alkyl, C$_{3-7}$ cycloalkyl, aryl, aryl(C$_{1-6}$)alkyl, C$_{3-7}$ heterocycloalkyl, heteroaryl, heteroaryl(C$_{1-6}$)alkyl, C$_{1-6}$ alkoxy or C$_{1-6}$ alkylthio, any of which groups may be optionally substituted; and hydrogen, halogen, cyano, trifluoromethyl or —NR$^X$R$^y$, in which R$^X$ and R$^y$ are as defined above. Examples of optional substituents on the groups A$^1$, A$^2$ and R$^2$ suitably include trifluoromethyl, C$_{1-6}$ alkoxy, C$_{2-6}$ alkoxycarbonyl, C$_{2-6}$ alkylcarbonyl, C$_{1-6}$ alkylsulphonyl, arylsulphonyl, amino, mono- or di(C$_{1-6}$)alkylamino, C$_{2-6}$ alkylcarbonylamino, arylcarbonylamino, C$_{2-6}$ alkoxycarbonylamino, C$_{1-6}$ alkylsulphonylamino, arylsulphonylamino, C$_{1-6}$ alkylsulphonylaminomethyl, aminocarbonylamino, mono- or di(C$_{1-6}$) alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminosulphonylmethyl.

Particular values of $A^1$, $A^2$ and $R^2$ include hydrogen, methyl, methoxymethyl, aminomethyl, dimethylaminomethyl, acetylaminomethyl, benzoylaminomethyl, t-butoxycarbonylaminomethyl, methylsulphonylaminomethyl, phenylsulphonylaminomethyl, aminocarbonylmethyl, ethyl, aminoethyl, acetylaminoethyl, benzoylaminoethyl, methoxycarbonylaminoethyl, ethoxycarbonylaminoethyl, t-butoxycarbonylaminoethyl, methylsulphonylaminoethyl, aminocarbonylaminoethyl, methylaminocarbonylaminoethyl, t-butylaminocarbonylaminoethyl, phenylaminocarbonylaminoethyl, pyrrolidylcarbonylaminoethyl, cyclopropyl, phenyl, methylsulphonylaminophenyl, aminocarbonylphenyl, methylaminocarbonylphenyl, methylsulphonylaminomethyl-phenyl, aminosulphonylmethylphenyl, methylaminosulphonylmethylphenyl, dimethylaminosulphonylmethylphenyl, benzyl, trifluoromethylbenzyl, methoxybenzyl, acetylaminobenzyl, methylsulphonylaminobenzyl, aminocarbonylaminobenzyl, aminocarbonylbenzyl, methylaminocarbonylbenzyl, methylsulphonylbenzyl, methylaminosulphonylbenzyl, pyridylmethyl, methoxypyridylmethyl, amino, methylamino, benzylamino, dimethylamino, t-butoxycarbonylamino-ethylamino and methylsulphonylaminoethylamino.

Preferred values of $A^1$ and $A^2$ include hydrogen, methyl and ethyl.

Suitably, $R^2$ is hydrogen.

The heterocyclic ring containing the moiety N—$R^1$ is an azetidin-2-yl, azetidin-3-yl, pyrrolidin-2-yl, pyrrolidin-3-yl, piperidin-2-yl or piperidin-3-yl ring, in particular an azetidin-2-yl or pyrrolidin-2-yl ring, substituted on the ring nitrogen atom by the group $R^1$.

Suitable values for the substituent $R^1$ include $C_{1-6}$ alkoxy ($C_{1-6}$)alkyl, aryl($C_{1-6}$)alkyl and heteroaryl($C_{1-6}$)alkyl, any of which groups may be optionally substituted. Examples of optional substituents on the group $R^1$ include halogen, trifluoromethyl, hydroxy, $C_{1-6}$ alkoxy, $C_{2-6}$ alkoxycarbonyl, $C_{2-6}$ alkylcarbonylamino and $C_{2-6}$ alkoxycarbonylamino.

Particular values of $R^1$ include methoxyethyl, benzyl, acetylamino-benzyl, phenethyl and pyridylmethyl.

Preferred values for the groups $R^3$ and $R^4$ include hydrogen and methyl.

Particular sub-classes of compounds according to the invention are represented by the compounds of formulae IIA and IIB, and salts and prodrugs thereof:

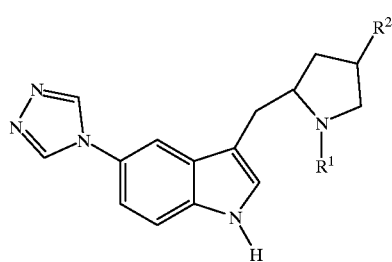

(IIA)

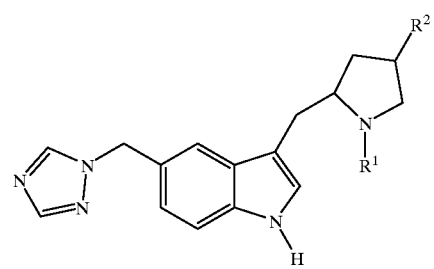

(IIB)

wherein $R^1$ and $R^2$ are as defined with reference to formula I above.

Specific compounds within the scope of the present invention include:
- (2R)-N-benzyl-2-[5-(1,2,4-triazol-4-yl)-1H-indol-3-yl] methylpyrrolidine;
- (2R)-N-(4-acetylaminobenzyl)-2-[5-(1,2,4-triazol-4-yl)-1H-indol-3-yl]methylpyrrolidine;
- (2R)-N-(3-pyridylmethyl)-2-[5-(1,2,4-triazol-4-yl)-1H-indol-3-yl]methylpyrrolidine;
- (2R)-N-(2-phenylethyl)-2-[5-(1,2,4-triazol-4-yl)-1H-indol-3-yl]methylpyrrolidine;
- (2R)-N-(2-methoxyethyl)-2-[5-(1,2,4-triazol-4-yl)-1H-indol-3-yl]methylpyrrolidine;
- (2S)-N-benzyl-2-[5-(1,2,4-triazol-4-yl)-1H-indol-3-yl] methylpyrrolidine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to this invention may be prepared by a process which comprises reacting a compound of formula III with a compound of formula IV:

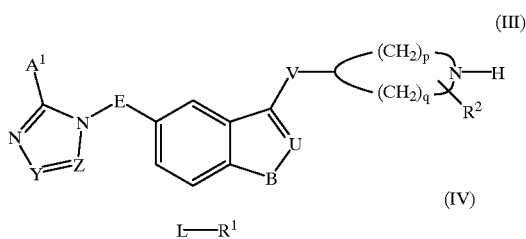

(III)

(IV)

wherein $A^1$, Y, Z, E, B, U, V, p, q, $R^1$ and $R^2$ are as defined above, and L represents a suitable leaving group.

The leaving group L is suitably a halogen atom, e.g. bromine or iodine.

The reaction is conveniently carried out by stirring the reactants under basic conditions in a suitable solvent, for example in a dimethoxyethane and N,N-dimethylformamide solvent system in the presence of sodium carbonate, typically at the reflux temperature of the solvent.

In an alternative procedure, the compounds according to the invention represented by formula V:

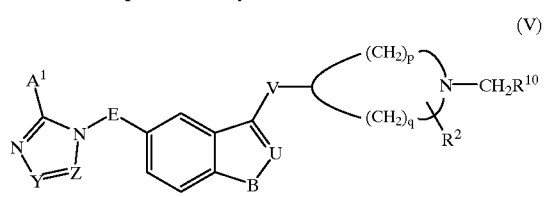

(V)

wherein $A^1$, Y, Z, E, B, U, V, p, q and $R^2$ are as defined above, and —$CH_2R^{10}$ corresponds to a group of formula $R^1$ as defined above; may be prepared by a reductive amination process which comprises reacting a compound of formula III as defined above with an aldehyde derivative of formula $R^{10}$—CHO in the presence of a reducing agent.

An appropriate reducing agent for use in this procedure is sodium cyanoborohydride, in which case the reaction is conveniently carried out in an alcoholic solvent such as methanol, typically in the presence of acetic acid.

In a further procedure, the compounds according to the invention wherein the group F is an indole moiety of structure FC as defined above may be prepared by reacting a compound of formula VI:

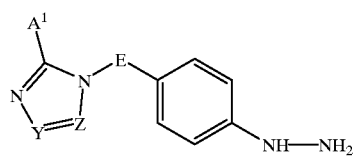

(VI)

wherein $A^1$, Y, Z and E are as defined above; with a compound of formula VII or a carbonyl-protected form thereof:

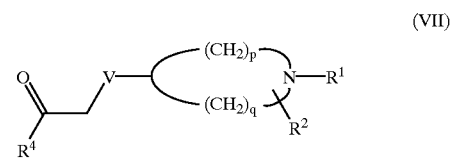

(VII)

wherein V, p, q, $R^1$, $R^2$ and $R^4$ are as defined above; and subsequently, where required, N-alkylation by standard methods to introduce the moiety $R^3$.

Suitable carbonyl-protected forms of the compounds of formula VII include the dimethyl acetal or ketal derivatives.

The reaction of compounds VI and VII may be carried out in a single step (Fischer indole synthesis) or by an initial non-cyclising step at a lower temperature to give a compound of formula VIII:

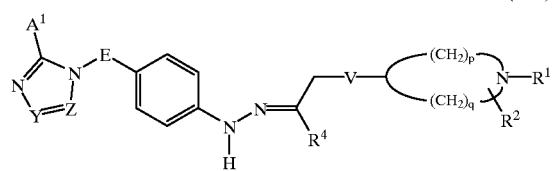

(VIII)

wherein $A^1$, Y, Z, E, V, p, q, $R^1$, $R^2$ and $R^4$ are as defined above; followed by cyclisation using a suitable reagent, such as a polyphosphate ester.

The hydrazines of formula VI may be prepared from the corresponding anilines of formula IX:

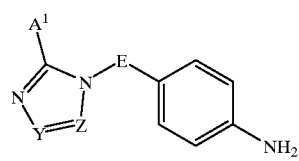

(IX)

wherein $A^1$, Y, Z and E are as defined above; by diazotisation followed by reduction. Diazotisation is typically carried out using sodium nitrite/conc. HCl and the resulting diazo product reduced in situ using, for example, tin(II) chloride/conc. HCl, sodium sulphite/conc. HCl, or sodium sulphite/conc. $H_2SO_4$.

The anilines of formula IX may be prepared by reduction of the corresponding nitro compounds of formula X:

(X)

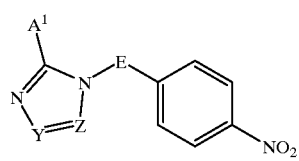

wherein $A^1$, Y, Z and E are as defined above; typically by transfer hydrogenation using a hydrogenation catalyst such as palladium on charcoal in the presence of a hydrogen donor such as ammonium formate, or alternatively by conventional catalytic hydrogenation or using tin(II) chloride.

In a still further process, the compounds according to the invention wherein the group F is an indazole moiety of structure FB as defined above may be prepared by the cyclisation of a compound of formula XI:

(XI)

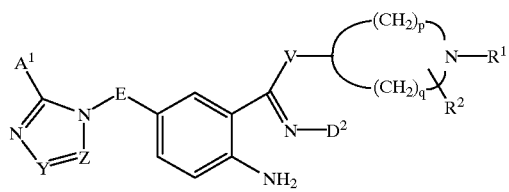

wherein $A^1$, Y, Z, E, V, p, q, $R^1$ and $R^2$ are as defined above and $D^2$ represents a readily displaceable group; and subsequently, where required, N-alkylation by standard methods to introduce the moiety $R^3$.

The cyclisation of compound XI is conveniently achieved in a suitable organic solvent at an elevated temperature, for example in a mixture of m-xylene and 2,6-lutidine at a temperature in the region of 140° C.

The readily displaceable group $D^2$ in the compounds of formula XI suitably represents a $C_{1-4}$ alkanoyloxy group, preferably acetoxy. Where $D^2$ in the desired compound of formula XI represents acetoxy, this compound may be conveniently prepared by treating a carbonyl compound of formula XII:

(XII)

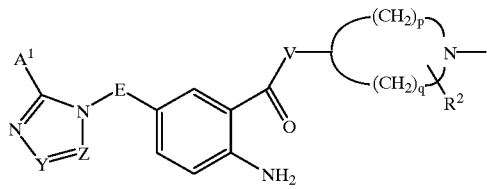

wherein $A^1$, Y, Z, E, V, p, q, $R^1$ and $R^2$ are as defined above; or a protected derivative thereof; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivative of the intermediate of formula XII may be conveniently prepared by ozonolysis of an indole derivative of formula XIII:

(XIII)

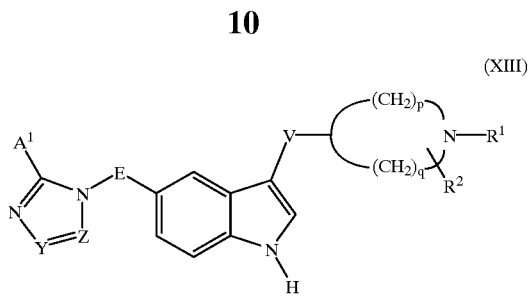

wherein $A^1$, Y, Z, E, V, p, q, $R^1$ and $R^2$ are as defined above; followed by a reductive work-up, advantageously using dimethylsulphide.

The indole derivative of formula XIII may be prepared by methods analogous to those described in the accompanying Examples, or by procedures well known from the art.

In an alternative process, the triazole compounds according to the invention may be prepared by a method which comprises reacting a compound of formula XIV:

(XIV)

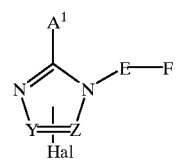

wherein $A^1$, Y, Z, E and F are as defined above, and Hal represents halogen; with a reagent which provides an anion $^-$A2, where $A^2$ is as previously defined.

Reagents which may provide the anion $^-$A2 include Grignard reagents A2MgHal (where Hal=halogen); organocuprate reagents such as $LiA^2{}_2Cu$; organolithium reagents $A^2Li$; or compounds which stabilise the anion by means of an adjacent activating group such as an ester or enolisable ketone function. In this case, the adjacent ester or ketone function may be retained after the process is complete, or may be removed. For example, an ester moiety may be hydrolysed and decarboxylated.

The intermediates of formula III above may be prepared by reacting a compound of formula VI as defined above with a compound of formula XV, or a carbonyl-protected form thereof:

(XV)

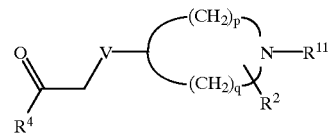

wherein V, p, q, $R^2$ and $R^4$ are as defined above, and $R^{11}$ represents hydrogen or an amino-protecting group; followed, where required, by removal of the amino-protecting group $R^{11}$.

As for compound VII, suitable carbonyl-protected forms of the compounds of formula XV include the dimethyl acetal and ketal derivatives.

The amino-protecting group $R^{11}$, where present, is suitably a lower alkoxycarbonyl moiety such as t-butoxycarbonyl (BOC), which can be conveniently removed as necessary by treatment with acid.

As with that between compounds VI and VII, the reaction between compounds VI and XV may be carried out in a single step (Fischer indole synthesis) or by an initial non-cyclising step at a lower temperature to give a compound of formula XVI:

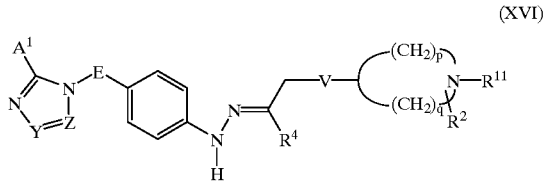
(XVI)

wherein Y, Z, $A^1$, E, V, p, q, $R^2$, $R^4$ and $R^{11}$ are as defined above; followed by cyclisation using a suitable reagent, e.g. a polyphosphate ester.

The nitro compounds of formula X may be prepared by a variety of methods which will be readily apparent to those skilled in the art. For example, the relevant compounds of formula X may be prepared by reacting the anion of a compound of formula XVII with a compound of formula XVIII:

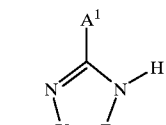
(XVII)

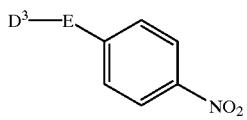
(XVIII)

wherein Y, Z, $A^1$ and E are as defined above, and $D^3$ represents a readily displaceable group.

The anion of compound XVII may be generated by carrying out the reaction in a base such as triethylamine. Where salts of the compounds of formula XVII are commercially available, e.g. the sodium salt of 1,2,4-triazole, these are advantageously utilised in N,N-dimethylformamide solution in place of the compounds of formula XVII themselves, with no requirement in this instance for additional base to be present in the reaction mixture.

The readily displaceable group $D^3$ in the compounds of formula XVIII is suitably a halogen atom, preferably bromine; except when the moiety $D^3$ is attached directly to the aromatic ring, i.e. when E represents a bond, in which case $D^3$ is preferably fluorine.

In an alternative approach, the compounds of formula X wherein the five-membered heteroaromatic ring is a 1,2,4-triazol-1-yl moiety and $A^1$ and $A^2$ are both hydrogen may be prepared by reacting 4-amino-1,2,4-triazole with a compound of formula XVIII as defined above, followed by deamination of the resulting 1-substituted 4-amino-4H-1,2, 4-triazolium salt by treatment with nitrous acid and subsequent neutralisation. This transformation, which may be accomplished in two separate steps or advantageously as a "one-pot" procedure with both steps combined, is conveniently effected using reaction conditions analogous to those described in *J. Org. Chem.*, 1989, 54, 731.

Where they are not commercially available, the nitro compounds of formula XVIII above may be prepared by methods well known from the art.

Following a further representative pathway, the aniline derivatives of formula IX wherein the five-membered heteroaromatic ring is a 1,2,4-triazol-4-yl moiety, E is a bond and $A^1$ and $A^2$ are both hydrogen may be prepared by reacting the hydrazine derivative of formula XIX with the acetanilide of formula XX:

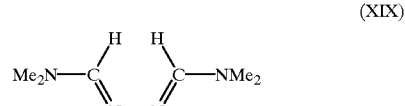
(XIX)

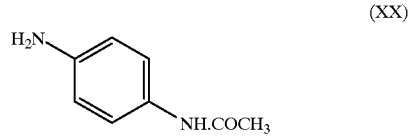
(XX)

followed by removal of the N-acetyl protecting group.

The reaction between compounds XIX and XX is conveniently effected in refluxing toluene, advantageously in the presence of a catalytic quantity of p-toluenesulphonic acid, subsequent removal of the N-acetyl protecting group is typically effected in hot aqueous 5N hydrochloric acid.

The hydrazine derivative of formula XIX can be prepared from N,N'-diformylhydrazine by reaction with thionyl chloride/N,N-dimethylformamide, as reported in *J. Chem. Soc. (C)*, 1967, 1664, and subsequent treatment with sodium methoxide in methanol.

The acetanilide of formula XX may be prepared by reduction of the corresponding nitro compound of formula XXI:

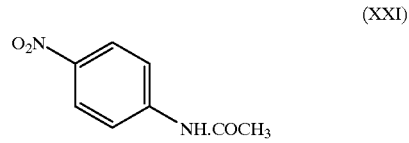
(XXI)

typically by transfer hydrogenation using a hydrogenation catalyst in the presence of a hydrogen donor such as ammonium formate, or alternatively by conventional catalytic hydrogenation or using tin(II) chloride.

The nitro compound of formula XXI is commercially available from the Aldrich Chemical Company Ltd., Gillingham, United Kingdom.

In a yet further process, the compounds according to the invention wherein the group F is a benzofuran or benzthiophene moiety may be prepared by a method which comprises cyclising a compound of formula XXII:

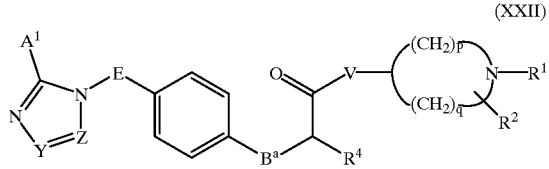
(XXII)

wherein Y, Z, $A^1$, E, V, p, q, $R^1$, $R^2$ and $R^4$ are as defined above, and $B^a$ represents oxygen or sulphur.

The cyclisation is conveniently effected by using polyphosphoric acid or a polyphosphate ester, advantageously at an elevated temperature.

The compounds of formula XXII may be prepared by reacting a compound of formula XXIII with a compound of formula XXIV:

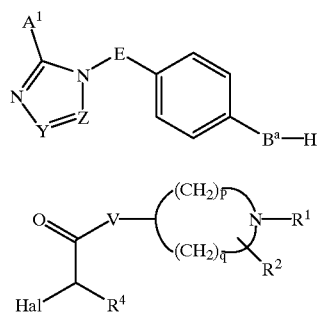

(XXIII)

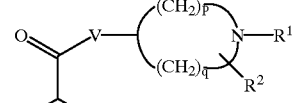

(XXIV)

wherein Y, Z, A¹, E, $B^a$, V, p, q, R¹, R² and R⁴ are as defined above, and Hal represents halogen.

The reaction is conveniently effected in the presence of a base such as sodium hydroxide.

The hydroxy and mercapto derivatives of formula XXIII may be prepared by a variety of methods which will be readily apparent to those skilled in the art. In one such method, the anion of a compound of formula XVII as defined above is reacted with a compound of formula XXV:

(XXV)

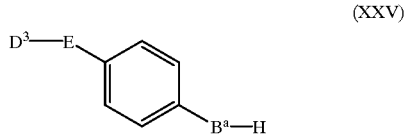

wherein $D^3$, E and $B^a$ are as defined above.

The compounds of formula XXIV and XXV, where they are not commercially available, may be prepared by standard procedures well known in the art.

The preparation of a typical intermediate of formula XV, protected on the ring nitrogen atom by a BOC group, is illustrated by the following reaction scheme:

(XXVI)

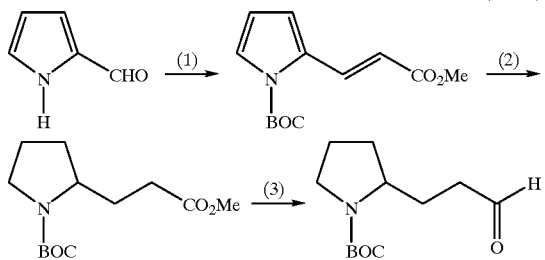

The starting compound XXVI is commercially available from Aldrich Chemical Company Ltd., Gillingham, U.K. Step 1 of the reaction scheme involves protection of the pyrrole nitrogen as the N-t-butoxycarbonyl (N-BOC) carbamate derivative; followed by reaction of the formyl moiety in the 2-position with the Horner-Emmons reagent $MeO_2C.CH_2.PO(OEt)_2$ in the presence of sodium hydride, using THF as the solvent. In Step 2, the pyrrole and exocyclic double bonds are hydrogenated over platinum oxide in acetic acid. This is followed in Step 3 by partial reduction of the side-chain methyl ester group to an aldehyde moiety using DIBAL-H in THF at –80° C.

In a variant of the reaction scheme described immediately above, the preparation of a chiral intermediate of formula XV, comprising a pyrrolidinyl moiety having a chiral centre at the 2-position and protected on the ring nitrogen atom by a BOC group, is illustrated by the following reaction scheme:

(XXVII)

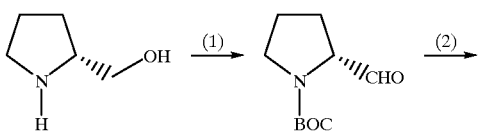

(XXVIII)

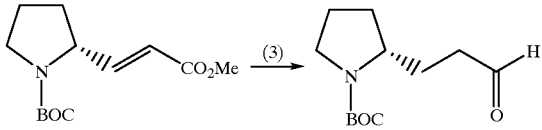

The starting compound XXVII, D-prolinol, is commercially available from Aldrich Chemical Company Ltd., Gillingham, U.K. Step 1 of the reaction scheme involves protection of the pyrrolidine nitrogen as the N-BOC derivative, typically using BOC anhydride in dichloromethane; followed by Swern oxidation (oxalyl chloride/dimethyl sulphoxide/dichloromethane/–78° C., then triethylamine) of the terminal hydroxy group to an aldehyde moiety. Step 2 involves reaction with the Horner-Emmons reagent $MeO_2C.CH_2.PO(OEt)_2$ in the presence of sodium hydride, using THF as the solvent. In Step 3 the side-chain double bond is reduced, conveniently by catalytic hydrogenation over palladium-charcoal in aqueous methanol; and the methyl ester moiety is then partially reduced to an aldehyde functionality using DIBAL-H in THF at –78° C., to give the desired product of formula XXVIII.

As will be appreciated, the compound corresponding to compound XXVIII, but having the opposite stereochemistry at the 2-position of the pyrrolidine ring, is readily obtainable, using an identical sequence of steps, from L-prolinol (i.e. the opposite antipode of compound XXVII), which is also commercially available from Aldrich Chemical Company Ltd.

It will be understood that any compound of formula I initially obtained from any of the above processes may, where appropriate, subsequently be elaborated into a further compound of formula I by techniques known from the art. In particular, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (–)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The ability of test compounds to bind to 5-HT$_1$-like receptors was measured in membranes prepared from pig caudate using the procedure described in *J. Neurosci.*, 1987, 7, 894. Binding was determined using 2 nM 5-hydroxytryptamine creatinine sulphate, 5-[1,2-$^3$H(N)] as a radioligand. Cyanopindolol (100 nM) and mesulergine (100 nM) were included in the assay to block out 5-HT$_{1A}$ and 5-HT$_{1C}$ binding sites respectively. The concentration of the compounds of the accompanying Examples required to displace 50% of the specific binding (IC$_{50}$) is below 1 μM in each case.

The activity of test compounds as agonists of the 5-HT$_1$-like receptor was measured in terms of their ability to mediate contraction of the saphenous vein of New Zealand White rabbits, using the procedure described in *Arch. Pharm.*, 1990, 342, 111. Agonist potencies were calculated as -log$_{10}$EC$_{50}$ (pEC$_{50}$) values, from plots of percentage 5-HT (1 μM) response against the concentration of the agonist. The compounds of the accompanying Examples were found to possess pEC$_{50}$ values in this assay of not less than 5.0 in each case.

EXAMPLE 1
(2R)-N-Benzyl-2-[5-(1,2,4-triazol-4-yl)-1H-indol-3-yl] methylpyrrolidine. Oxalate. 0.7 Hydrate INTERMEDIATE 1
4'-(1,2,4-Triazol-4-yl)phenylhydrazine
 1. 4'-Aminoacetanilide
 A solution of 4'-nitroacetanilide (5.0g, 27.8mmol) in EtOH/EtOAc (160ml, 1:1), H$_2$O (15ml) and 5N HCl (5.6ml, 28.0 mmol) was hydrogenated over 10% Pd-C (0.50g) at 50 psi for 0.25h. The catalyst was removed by filtration through celite and the solvents removed under vacuum. The free base was generated by dissolving the product in H$_2$O, basifying with 2N NaOH and extracting into EtOAc. The combined extracts were dried (MgSO$_4$) and evaporated to give the title-aniline (3.75g, 90%); $^1$H NMR (250 MHz, CDCl$_3$/d$_4$-MeOH) δ 2.10 (3H, s, CH$_3$), 6.68 (2H, d, J=8.8Hz, Ar—H), 7.27 (2H, d, J=8.8 Hz, Ar—H).
 2. 4'-(1,2,4-Triazol-4-yl)acetanilide
 A mixture of the preceding aniline (3.52 g, 23.4 mmol), N,N-dimethylformamide azine (3.33 g, 23.4 mmol; *J. Chem. Soc. (C)* 1967, 1664) and p-toluenesulphonic acid monohydrate (0.223 g, 1.17 mmol), in anhydrous toluene (100 ml), was heated at reflux for 17 h. The beige coloured precipitate was filtered off and washed with toluene and CH$_2$Cl$_2$ and dried under vacuum to give the desired triazole (4.29 g, 91%); $^1$H NMR (250 MHz, d$_4$-MeOH/d$_6$-DMSO) δ 2.14 (3H, s, CH$_3$), 7.60 (2H, d, J=8.8 Hz, Ar—H), 7.78 (2H, d, J=8.8 Hz, Ar—H), 8.96 (2H, s, Ar—H).
 3. 4'-(1,2,4-Triazol-4-yl)phenylaniline
 A solution of the preceding acetanilide (4.91 g, 24.3 mmol) in 5N HCl (100 ml) was heated at 125° C. for 1.5 h. The mixture was cooled to 0° C., basified with concentrated aqueous NaOH solution and extracted with CH$_2$Cl$_2$ (×5). The combined extracts were dried (MgSO$_4$) and evaporated and the residue chromatographed on silica gel, eluting with CH$_2$Cl$_2$/MeOH/NH$_3$ (80:8:1), to give the title-aniline (2.94 g, 76%); $^1$H NMR (250 MHz, CDCl$_3$) δ 3.80 (2H, s, NH$_2$), 6.71 (2H, d, J=8.8Hz, Ar—H), 7.08 (2H, d, J=8.8Hz, Ar—H), 8.36 (2H, s, Ar—H).
 4. 4'-(1,2,4-Triazol-4-yl)phenylhydrazine
 To a solution of the preceding aniline (1.60 g, 9.99 mmol) in concentrated HCl/H$_2$O (23 ml and 3 ml respectively) was added, at -21° C., a solution of NaNO$_2$ (0.69 g, 9.99 mmol) in H$_2$O (8 ml), at such a rate as to maintain the temperature below -10° C. The mixture was stirred for 0.3 h and then filtered rapidly through a sinter, under vacuum. The filtrate was added to a cooled (-20° C.) solution of SnCl$_2$.2H$_2$O (9.02 g, 40.0 mmol) in concentrated HCl (17 ml). The mixture was stirred at -20° C. for 0.25 h and then at room temperature for 1.25 h. The resulting solid was filtered off, washed with Et$_2$O and dried under vacuum. The crude product was dissolved in H$_2$O, basified with concentrated aqueous NaOH and extracted with EtOAc (×5). The combined extracts were dried (MgSO$_4$) and evaporated to afford the title-product (0.95 g, 54%); $^1$H NMR (250 MHz, CDCl$_3$/d$_4$-MeOH) δ 3.98 (3H, br s, NH and NH$_2$); 6.97 (2H, d, J=12.0 Hz, Ar—H); 7.25 (2H, d, J=12.0Hz, Ar—H); 8.48 (2H, s, Ar—H).

INTERMEDIATE 2
(2R)-N-tert-Butyloxycarbonyl-3-pyrrolidin-2-yl)propanal
 1. (2R)-N-tert-Butyloxycarbonylpyrrolidin-2-ylmethanol
 A solution of di-tert-butyl dicarbonate (34.11 g, 156.3 mmol) in DCM (125 ml) was added dropwise to a stirred solution of D-prolinol (15.04 g, 148.7 mmol) in CH$_2$Cl$_2$ (125ml) at 0° C. under nitrogen. The mixture was stirred at 0° C. for 1 h and then at room temperature for 66 h. Evaporation of the solvent afforded the title-carbamate (29.9 g, 100%); $^1$H NMR (360 MHz, CDCl$_3$) δ 1.47 (9H, s, $^t$Bu), 1.60 (1H, br m, CH$_2$), 1.72–1.89 (2H, m, CH$_2$), 2.00 (1H, m, CH$_2$), 3.31 (1H, m, CH$_2$), 3.46 (1H, m, CH$_2$), 3.55–3.66 (2H, m, CH$_2$), 3.95 (1H, br m, CH$_2$).
 2. (2R)-N-tert-Butyloxycarbonylpyrrolidin-2-vlmethanal
 DMSO (8.63 ml, 122 mmol) was added dropwise to a stirred solution of oxalyl chloride (5.31 ml, 60.9 mmol) in CH$_2$Cl$_2$ (350 ml) at -78° C. under nitrogen. The mixture was stirred at this temperature for 30 mins before adding a solution of the preceding alcohol (10.20 g, 50.68 mmol) in CH$_2$Cl$_2$ (120 ml). After stirring at -78° C. for 95 mins, triethylamine (35.5 ml, 255 mmol) was added dropwise and the mixture allowed to warm to room temperature. Water was added, the mixture extracted with CH$_2$Cl$_2$ and the combined extracts dried (MgSO$_4$) and evaporated. The residue was purified by flash chromatography on silica gel, eluting with 1:1 ethyl acetate/hexane, to afford the title—aldehyde (10.1 g, 100%); $^1$H NMR (360 MHz, CDCl$_3$) δ 1.38 and 1.41 (9H, 2 x s, $^t$Bu), 1.79–2.06 (4H, m, CH$_2$), 3.39–3.48 (2H, m, CH$_2$), 3.98 and 4.14 (1H, 2 x m, CH$_2$), 9.40 and 9.49 (1H, 2 x s, CHO).
 3.(2R)-trans-Methyl[N-tert-butyloxy carbonyl-3-(pyrrolidin-2-yl)] propenoate
 Methyl diethylphosphonoacetate (3.71, 20.2 mmol) was added dropwise to a stirred suspension of sodium hydride (0.81 g, 60% dispersion ill oil, 20.3 mmol) in THF (30 ml) at 4° C. under nitrogen. The mixture was stirred at room temperature for 0.5 h, recooled to 2° C. and a solution of the preceding aldehyde (4.03 g, 20.2 mmol) in THF (35 ml) added dropwise, maintaining the temperature below 10° C. The mixture was stirred at 7.5° C. for 2.5 h before evaporating the solvent in vacuo and redissolving the residue in CH$_2$Cl$_2$. The solution was washed with water (×1), 20% w/v sodium bisulphite solution (×2) and water (×1), dried (MgSO$_4$) and evaporated. Flash chromatography on silica gel of the residue, eluting with 40:60 ethyl acetate/hexane, afforded the title—ester (4.92 g, 95%); $^1$H NMR (360 MHz, CDCl$_3$) δ 1.42 (9H, br s, $^t$Bu), 1.78–1.88 (3H, m, CH$_2$), 2.08 (1H, m, CH), 3.44 (2H, br s, CH$_2$), 3.74 (3H, s, CO$_2$Me), 4.37–4.50 (1H, m, CH), 5.83 (1H, d, J=15.2 Hz, vinyl CH), 6.83 (1H, m, vinyl CH).

4. (2R)-Methyl [N-tert-butyloxy carbonyl-3-(pyrrolidin-2-yl) propanoate

A mixture of the preceding olefinic ester (4.34 g, 17.0 mmol) 10% Pd/C (0.43 g), methanol (30 ml) and water (10 ml) was hydrogenated on a Parr shake apparatus for 2 h. The catalyst was removed by filtration through celite and the solvents evaporated in vacuo. Flash chromatography of the residue on silica gel, eluting with 30:70 ethyl acetate/hexane, afforded the title—ester (4.21 g, 96%); [α]$_D$+36.5° (c 0.37, CH$_2$Cl$_2$); $^1$H NMR (360 MHz, CDCl$_3$) δ 1.46 (9H, s, $^t$Bu), 1.54–2.02 (6H, m, CH$_2$), 2.33 (2H, t, J=7.8 Hz, m, CH$_2$), 3.29 (1H, m, CH$_2$), 3.39 (1H, m, CH$_2$), 3.67 (3H, s, CO$_2$Me), 3.81 (1H, m, CH).

5. (2R)-N-tert-Butyloxycarbonyl-3-(pyrrolidin-2-yl) propanal

Diisobutylaluminium hydride (9.45 ml of a 1.0 M solution in toluene, 9.45 mmol) was added dropwise to a stirred solution of the preceding ester (1.62 g, 6.30 mmol) at −78° C. under nitrogen, at such a rate as to maintain the temperature below −75° C. After the addition was complete, the mixture was stirred at −75° C. for 4.25 h before adding MeOH (0.95 ml), H$_2$O (0.95 ml) and sodium hydroxide solution (2N, 0.95 ml), successively, dropwise. The mixture was warmed to room temperature and the precipitated salts removed by filtration through celite. The solvent was evaporated in vacuo and the residue chromatographed on silica gel, eluting with ethyl acetate/hexane (3:4) to give the title—aldehyde (0.86 g, 60%); $^1$H NMR (250 MHz, CDCl$_3$) δ 1.46 (9H, S, $^t$Bu), 1.58–1.99 (6H, m, CH$_2$), 2.45 (2H, dt, J=1.2 and 7.5 Hz, CH2—CHO), 3.25–3.39 (2H, m, CH$_2$), 3.83 (1H, m, CH), 9.76 (1H, t, J=1.2 Hz, CHO).

INTERMEDIATE 3
(2R)-2-[5-(1,2,4-Triazol-4-yl)-1H-indol-3-yl]methyl pyrrolidine

A solution of 4'-(1,2,4-triazol-4-yl)phenylhydrazine dihydrochloride (1.12 g, 4.49 mmol) and (2R)-N-tert-butyloxycarbonyl-3-(pyrrolidin-2-yl)propanal (0.847 g, 3.73 mmol) in 4% aqueous sulphuric acid (80 ml) was stirred at room temperature for 0.5 h and then heated at reflux for 25 h. After cooling to room temperature, n-butanol was added and the aqueous basified with saturated aqueous potassium carbonate solution. The aqueous was separated and extracted further with n-butanol (×2). The combined organics were evaporated in vacuo and the residue flash chromatographed on silica gel eluting with CH$_2$Cl$_2$/MeOH/NH$_3$ (20:8:1), to give the title—pyrrolidine (0.263 g, 26%); $^1$H NMR (360 MHz, d$^4$-MeOH) δ 1.47 (1H, m, CH$_2$), 1.68–1.94 (3H, m, CH$_2$), 2.61 (1H, m, CH), 2.92 (2H, d, J=6.8 Hz, CH$_2$), 3.01 (1H, m, CH$_2$), 3.42 (1H, pentet, J=7.4 Hz, CH), 7.19–7.22 (2H, m, Ar—H), 7.43 (1H, d, J=8.7Hz, Ar—H), 7.71 (1H, d, J=1.8Hz, Ar—H), 8.82 (2H, s, Ar—H).

(2R)-N-Benzyl-2-[5-(1,2,4-triazol-4-yl)-1H-indol-3-yl]methylpyrrolidine. Oxalate. 0.7 Hydrate To a cooled solution of Intermediate 3 (272 mg, 1.02 mmol), NaCNBH$_3$ (77 mg, 1.22 mmol) and acetic acid (0.15 ml, 2.55 mmol) in methanol (30 ml) was added a solution of benzaldehyde (0.13 ml, 1.27 mmol) in methanol (10 ml). The mixture was stirred at 0° C. for 1.25 h and then warmed to room temperature and stirred for 2 h before adding a further portion of NaCNBH$_3$ (45 mg, 0.72 mmol). Saturated K$_2$CO$_3$ solution was added and the solvent removed in vacuo. The aqueous was extracted with EtOAc (×3) and the combined extracts dried (MgSO$_4$) and the solvent evaporated in vacuo. The crude product was chromatographed on silica gel, eluting with CH$_2$Cl$_2$/MeOH/NH$_3$ (70:8:1) to give the title product. The oxalate salt was prepared which crystallised out containing a small amount of ether; m.p. 116–118° C.; (Found: C, 62.49; H, 5.75; N, 15.01. C$_{22}$H$_{23}$N$_5$.1.0.(C$_2$H$_2$O$_4$). 0.7(H$_2$O).0.2(C$_4$H$_{10}$O) requires C, 62.48; H, 6.04; N, 14.70%); $^1$H NMR (360 MHz, D$_2$O) δ 1.99 (1H, m, CH$_2$), 2.13–2.18 (2H, m, CH$_2$), 2.33 (1H, m, CH$_2$), 3.09–2.94 (2H, m, CH$_2$), 3.35 (1H, m, CH), 3.70 (1H, m, CH$_2$), 3.93 (1H, m, CH), 4.09 (1H, d, J=13.1 Hz, CH$_2$Ar), 4.24 (1H, d, J=13.1 Hz, CH2Ar), 7.10–7.16 (6H, m, Ar—H), 7.25 (1H, dd, J=8.6 and 2.0 Hz, Ar—H), 7.34 (1H, s, Ar—H), 7.54 (1H, d, J=8.7 Hz), 8.76 (2H, s, Ar—H).

EXAMPLE 2
(2R)-N-(4-(Acetylamino)benzyl-2-[5-(1,2,4-triazol-4-yl)-1H-indol-3-yl]methylpyrrolidine. 1.2 Oxalate Hydrate Prepared from Intermediate 3 and 4-acetamidobenzaldehyde as described for Example 1. The oxalate salt was prepared which crystallised out containing a small amount of ether, m.p. 149–151° C.; (Found: C, 58.90; H, 5.75; N, 15.32. C$_{24}$H$_{26}$N$_6$O. 1.2(C$_2$H$_2$O$_4$).H$_2$O.0.1 (C$_4$H$_{10}$O) requires C, 58.74; H, 5.78; N, 15.34%); $^1$H NMR (360 MHz, D$_2$O) δ 2.00–2.08 (4H, m, CH$_3$+1 of CH$_2$), 2.26 (1H, m, CH$_2$), 2.47 (1H, m, CH$_2$), 2.93 (1H, dd, J=14.8 and 10.2 Hz, CH$_2$), 3.04 (1H, dd, J=15.3 and 4.8 Hz, CH$_2$), 3.40 (1H, m, CH$_2$), 3.82 (1H, m, CH$_2$), 3.98–4.01 (2H, br d, J=13.1Hz, 1 of CH$_2$Ar and 1 of CH), 4.21 (1H, d, J=13.1 Hz, CH$_2$Ar), 6.96 (2H, d, J=8.5 Hz, Ar—H), 7.05 (2H, d, J=8.4Hz, Ar—H), 7.14 (1H, s, Ar—H), 7.21 (1H, d, J=8.7 Hz, Ar—H), 7.32 (1H, s, Ar—H), 7.49 (1H, d, J=8.7 Hz, Ar—H), 8.76 (2H, s, Ar—H).

EXAMPLE 3
(2R)-N-(3-Pyridinyl)-2-[5-(1,2,4-triazol-4-yl)-1H-indol-3-yl]methylpyrrolidine. 3 Oxalate. 1.2 Hydrate Prepared from Intermediate 3 and 3-pyridinecarboxaldehyde as described for Example 1. The oxalate salt was prepared which crystallised out containing a small amount of ether, m.p. 113–115° C.; (Found C, 50.20; H, 4.65; N, 12.78. C$_{21}$H$_{22}$N$_6$. 3(C$_2$H$_2$O$_4$). 1.2(H$_2$O) 0.08 (C$_4$H$_{10}$O) requires C, 50.01; H, 4.79; N, 12.81%); 1H NMR (360 MHz, D$_2$O) δ 2.11 (1H, m, CH$_2$), 2.24–2.28 (2H, m, CH$_2$), 2.57 (1H, m, CH$_2$), 3.08–3.22 (2H, m, CH$_2$), 3.49 (1H, m, CH$_2$), 3.92 (1H, m, CH$_2$), 4.06 (1H, m, CH), 4.37 (1H, d, J=13.9 Hz, CH$_2$Ar), 4.53 (1H, d, J=13.8 Hz, CH$_2$Ar), 7.38–7.41 (2H, m, Ar—H), 7.53–7.58 (3H, m, Ar—H), 8.23 (1H, d, J=8.0Hz, Ar—H), 8.33 (1H, d, J=5.5 Hz, Ar—H), 8.45 (1H, s, Ar—H), 9.12 (2H, s, Ar—H).

EXAMPLE 4
(2R)-N-(2-Phenethyl -2-[5-(1,2,4-triazol-4-yl)-1H-indol-3-yl]methylpyrrolidine. 2.4 Oxalate. 1.2 Hydrate Prepared from Intermediate 3 and phenylacetaldehyde as described for Example 1. The oxalate salt was prepared, m.p. 73–75° C.; (Found: C, 54.68; H, 4.99; N, 11.49. C$_{23}$H$_{25}$N$_5$. 2.4(C$_2$H$_2$O$_4$). 1.2(H$_2$O) requires C, 54.81; H, 5.33; N, 11.50%); $^1$H NMR (360 MHz, D$_2$O) δ 1.93 (1H, m, CH$_2$), 2.06–2.13 (1H, m, CH$_2$), 2.35 (1H, m, CH$_2$), 2.78 (1H, m, CH$_2$), 2.91 (1H, m, CH), 3.14–3.28 (5H, m, CH), 3.78 (1H, m, CH$_2$), 3.94 (1H, qu, J=7.2 Hz, CH), 6.94–6.96 (2H, m, Ar—H), 7.28–7.29 (3H, m, Ar—H), 7.38–7.40 (2H, m, Ar—H), 7.70 (1H, d, J=8.7 Hz, Ar—H), 7.81 (1H, s, Ar—H), 9.09 (2H, s, Ar—H).

EXAMPLE 5

(2R)-N-(2-Methoxyethyl -2-[5-(1,2,4-triazol-4-yl)-1H-indol-3-yl]methylpyrrolidine. 1.75 Oxalate A mixture of Intermediate 3 (100 mg, 0.374 mmol), sodium carbonate (40 mg, 0.38 mmol), sodium iodide (62 mg, 0.41 mmol) and 2-bromomethoxyethane (0.035 ml, 0.37 mmol) in anhydrous DME (5 ml) was heated at reflux for 17 h. DMF (2 ml) was then added and the mixture boiled for a further 2.75 h. EtOAc (200 ml) was added and the mixture washed with saturated Na$_2$CO$_3$ solution (200 ml) and dried (MgSO$_4$). The solvent was evaporated in vacuo and the crude product chromatographed on silica gel, eluting with CH$_2$Cl$_2$/MeOH/NH$_3$ (80:8:1), to give the title—product. The oxalate salt was prepared, m.p. 68–70° C.; (Found: C, 53.22; H, 5.85; N, 14.43. C$_{18}$H$_{23}$N$_5$O.1.75(C$_2$H$_2$O$_4$) requires C, 53.47; H, 5.53; N, 14.50%); $^1$H NMR (360 MHz, D$_2$O) δ 1.92 (1H, m, CH$_2$), 2.05–2.10 (2H, m, CH$_2$), 2.26 (1H, m, CH$_2$), 3.17–3.46 (9H, m, CH$_3$O and CH$_2$), 3.56–3.66 (2H, m, CH$_2$), 3.78 (1H, m, CH$_2$), 3.92 (1H, qu, J=7.5 Hz, CH), 7.37 (1H, dd, J=8.6 and 1.9 Hz, Ar—H), 7.48 (1H, s, Ar—H), 7.66 (1H, d, J=8.7 Hz, Ar—H), 7.80 (1H, d, J=1.9 Hz, Ar—H), 9.02 (2H, s, Ar—H).

EXAMPLE 6

(2S)-N-Benzyl-2-[5-(1,2,4-triazol-4-yl)-1H-indol-3-yl] methylpyrrolidine. 1.2 Oxalate. Hydrate

INTERMEDIATE 4

(2S)-N-tert-Butyloxycarbonyl-3-(pyrrolidin-2-yl) propanal

Prepared from L-prolinol using the procedure described for Intermediate 2.

(2S)-2-[5-(1,2,4-Triazol-4-yl)-1H-indol-3-yl]methyl pyrrolidine

Prepared from Intermediate 1 and Intermediate 4 using the procedure described for Intermediate 3.

(2S)-N-Benzyl-2-[5-(1,2,4-triazol-4-yl)-1H-indol-3-yl] methylpyrrolidine. 1.2 Oxalate. Hydrate Prepared from the preceding NH-pyrrolidine using the procedure described for Example 1. The oxalate salt was prepared, m.p. 117–119° C.; (Found: C, 60.98; H, 5.37; N, 14.46. C$_{22}$H$_{23}$N$_5$.1.2(C$_2$H$_2$O). H$_2$O requires C, 61.26; H, 5.77; N, 14.76%); 1H NMR (360 MHz, D$_2$O) δ 2.00 (1H, m, CH$_2$), 2.17–2.20 (2H, m, CH$_2$), 2.33 (1H, m, CH$_2$), 2.92–3.08 (2H, m, CH), 3.37 (1H, m, CH$_2$), 3.72 (1H, m, CH$_2$), 3.92 (1H, m, CH), 4.10 (1H, d, J=13.1 Hz, C$\underline{H}_2$Ar), 4.27 (1H, d, J=13.1 Hz, C$\underline{H}_2$Ar), 7.05 (1H, d, J=1.8 Hz, Ar—H), 7.13–7.23 (6H, m, Ar—H), 7.35 (1H, s, Ar—H), 7.54 (1H, d, J=8.7 Hz, Ar—H), 8.72 (2H, m, Ar—H).

We claim:

1. A compound of formula IIA, or a salt thereof:

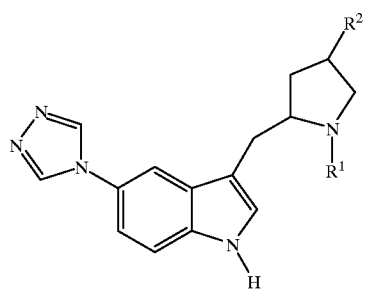

(IIA)

wherein

R$^1$ represents C$_{1-6}$ alkoxy(C$_{1-6}$)alkyl or aryl(C$_{1-6}$)alkyl, any of which groups may be optionally substituted by one or more groups selected from halogen, trifluoromethyl, hydroxy, C$_{1-6}$ alkoxy, C$_{2-6}$ alkoxycarbonyl, C$_{2-6}$ alkylcarbonylamino and C$_{2-6}$ alkoxycarbonylamino; the aryl moiety being phenyl; and R$^2$ represents hydrogen.

2. A compound as claimed in claim 1 wherein R$^1$ represents methoxyethyl, benzyl, acetylamino-benzyl or phenethyl.

3. A compound as claimed in claim 1 selected from:

(2R)-N-benzyl-2-[5-(1,2,4-triazol-4-yl)-1H-indol-3-yl] methylpyrrolidine;

(2R)-N-(4-acetylaminobenzyl)-2-[5-(1,2,4-triazol-4-yl)-1H-indol-3-yl]methylpyrrolidine;

(2R)-N-(2-phenylethyl)-2-[5-(1,2,4-triazol-4-yl)-1H-indol-3-yl]methylpyrrolidine;

(2R)-N-(2-methoxyethyl)-2-[5-(1,2,4-triazol-4-yl)-1H-indol-3-yl]methylpyrrolidine;

(2S)-N-benzyl-2-[5-(1,2,4-triazol-4-yl)-1H-indol-3-yl] methylpyrrolidine; or a salt thereof.

4. A pharmaceutical composition comprising a compound of formula IIA as defined in claim 1 or a pharmaceutically acceptable salt thereof in association with a pharmaceutically acceptable carrier.

5. A method for the treatment of migraine, cluster headache, chronic paroxysmal hemicrania, headache associated with vascular disorders, tension headache, and pediatric migraine, which comprises administering to a patient in need of such treatment an effective amount of a compound of formula IIA as defined in claim 1 or a pharmaceutically acceptable salt thereof.

* * * * *